United States Patent
Bera et al.

(10) Patent No.: US 7,485,603 B2
(45) Date of Patent: Feb. 3, 2009

(54) SOOT DISPERSANTS AND LUBRICATING OIL COMPOSITIONS CONTAINING SAME

(75) Inventors: Tushar K. Bera, Franklin Park, NJ (US); Nancy Z. Diggs, Westfield, NJ (US); Rolfe J. Hartley, Rockaway, NJ (US); Jacob Emert, Brooklyn, NY (US); Michael L. Alessi, Bedminster, NJ (US); Jun Hua, North Brunswick, NJ (US)

(73) Assignee: Infineum International Limited, Oxfordshire (GB)

( * ) Notice: Subject to any disclaimer, the term of this patent is extended or adjusted under 35 U.S.C. 154(b) by 552 days.

(21) Appl. No.: 11/061,800

(22) Filed: Feb. 18, 2005

(65) Prior Publication Data

US 2006/0189492 A1 Aug. 24, 2006

(51) Int. Cl.
*C10M 149/10* (2006.01)
*C10M 133/56* (2006.01)
*C10M 169/04* (2006.01)

(52) U.S. Cl. .............. 508/221; 508/454; 508/291

(58) Field of Classification Search ........... 508/221, 508/575, 454, 291

See application file for complete search history.

(56) References Cited

U.S. PATENT DOCUMENTS

| 1,815,022 | A | | 7/1931 | Davis |
| 2,686,164 | A | * | 8/1954 | Arvin et al. ................ 554/1 |
| 2,978,423 | A | | 4/1961 | Tirtiaux et al. |
| 3,035,908 | A | | 5/1962 | Gottshall et al. |
| 3,057,801 | A | | 10/1962 | Wilgus ..................... 252/59 |
| 3,737,465 | A | | 6/1973 | Karll et al. |
| 4,163,731 | A | * | 8/1979 | Randell et al. ............ 252/78.5 |
| 4,273,891 | A | | 6/1981 | Pindar et al. |
| 4,708,809 | A | | 11/1987 | Davis .................... 252/33.4 |
| 4,747,965 | A | * | 5/1988 | Wollenberg et al. ......... 508/291 |
| 4,751,258 | A | | 6/1988 | Minami ..................... 523/414 |
| 4,800,032 | A | | 1/1989 | Murphy ................. 252/51.5 A |
| 4,925,579 | A | * | 5/1990 | Stemke .................... 508/294 |
| 4,961,875 | A | | 10/1990 | Ohno et al. ............ 252/299.66 |
| 5,043,312 | A | | 8/1991 | Hiraishi et al. ............ 503/208 |
| 5,059,723 | A | | 10/1991 | Dressler .................... 568/45 |
| 5,137,980 | A | * | 8/1992 | DeGonia et al. ......... 525/327.6 |
| 5,652,201 | A | * | 7/1997 | Papay et al. ............... 508/228 |
| 5,679,871 | A | | 10/1997 | Nava ........................ 568/648 |
| 5,770,750 | A | | 6/1998 | Hutchings et al. |
| 5,821,202 | A | | 10/1998 | Forester et al. |
| 6,248,142 | B1 | | 6/2001 | Caprotti |
| 6,495,496 | B2 | | 12/2002 | Gutierrez et al. ........... 508/561 |
| 6,498,278 | B1 | | 12/2002 | Clements et al. ........... 568/630 |
| 6,750,183 | B2 | | 6/2004 | Gutierrez et al. ........... 508/329 |
| 2004/0014615 | A1 | * | 1/2004 | Gao et al. ................. 508/364 |
| 2004/0048753 | A1 | * | 3/2004 | Ritchie et al. .............. 508/232 |
| 2004/0242434 | A1 | * | 12/2004 | Yagishita et al. ........... 508/291 |

FOREIGN PATENT DOCUMENTS

| EP | 0 324 828 | 8/1992 |
| EP | 1387066 | 2/2004 |
| JP | 3-52838 | 3/1991 |
| JP | 2789693 | 8/1998 |
| JP | 2004107266 | 4/2004 |
| JP | 2789693 | 2/2006 |
| RO | 105571 | 9/1992 |
| RO | 105571 B1 * | 9/1992 |
| WO | WO 99/16852 | 4/1999 |
| WO | WO 01/16205 | 3/2001 |

OTHER PUBLICATIONS

STN File CA, Abstract 137:185296 & Huang, Q. et al. Organic Letters (2002) 4(15), 2505-2508 Abstract & CAS Registration No. 452056-08-5.
STN File CA, Abstract 128:114794 & CZ 282095 B6 (Vysoka Skola Chemicko-Technologicka) May 14, 1997 Abstract & CAS Registration No. 201297-12-3.
STN File CA, Abstract 122:80771 & Tso, H-W et al. Bulletin of the Institute of Chemistry, Academia Sinica (1994) 41, 25-32 Abstract & CAS Registration No. 160248-58-8.
STN File CA, Abstract 99:131407 & JP 58062638 A2 (Ricoh Co., Ltd.) Apr. 14, 1983 Abstract & CAS Registration No. 86727-33-5.

* cited by examiner

*Primary Examiner*—Glenn Caldarola
*Assistant Examiner*—Jim Goloboy

(57) ABSTRACT

Linked aromatic compounds found to act as potent soot dispersants in lubricating oil compositions; lubricating oil compositions containing such soot dispersants and precursor compounds from which the soot dispersants are derived.

48 Claims, No Drawings

SOOT DISPERSANTS AND LUBRICATING OIL COMPOSITIONS CONTAINING SAME

FIELD OF THE INVENTION

This invention relates to a novel class of linked aromatic compounds that act as potent soot dispersants in lubricating oil compositions and lubricating oil compositions containing same. More specifically, the invention is directed to compounds that, when added to lubricating oil compositions provide soot dispersing performance in the industry standard "Mack T11" engine test, with reduced levels of additive nitrogen. The invention is further directed to a novel class of precursor compounds from which such soot dispersants can be derived.

BACKGROUND OF THE INVENTION

Global Heavy Duty Diesel (HDD) engine emission legislation requires stepwise reductions in $NO_x$ and particulate emissions between 1989 and 2009. Many diesel engine manufacturers are now incorporating into HDD engines an Exhaust Gas Recirculation (EGR) system that is operated in a condensing mode for at least a portion of the time the engine is operated (e.g., at least 10% of the time the engine is operated), and retarding engine timing to reduce $NO_x$ and particulate emissions. In engines provided with a cooled EGR system, the EGR stream is cooled below the dew point of $NO_x$ and $SO_x$ and injected back into the engine under positive pressure. Under such conditions, water vapor condenses with the $NO_x$ and $SO_x$ to produce high levels of nitric and sulfuric acids in the recirculated exhaust gas stream. Under such conditions, unacceptable increases in the kinematic viscosity (kv) of lubricating oil compositions have been observed, even in the presence of relatively low levels of soot (e.g., 3 mass % soot).

Lubricating oil compositions comprise a major amount of base oil and additives that improve the performance and increase the useful life of the lubricant. Nitrogen-containing dispersants are commonly used lubricant additives. The function of a dispersant is to maintain in suspension within the oil, insoluble materials formed by oxidation and other mechanisms during use of the oil, to prevent sludge flocculation and precipitation of the insoluble materials. Another function of the dispersant is to reduce the agglomeration of soot particles, thus reducing increases in the viscosity of the lubricating oil upon use. In the severe environment of an engine provided with a cooled EGR system, it has been found that soot induced viscosity increase, as measured in a "Mack T-11" test cannot be controlled by conventional dispersants, even when the amount of such conventional dispersants are increased. Therefore, compounds providing potent soot dispersing properties and crankcase lubricants providing improved soot dispersing performance, have been continuously demanded.

U.S. Pat. No. 1,815,022 to Davis (1931) discloses condensates of naphthalene and essentially linear chlorinated waxes formed by Freidel Craft alkylation of the naphthalene. Such compounds are described as functioning as wax crystal modifiers or lube oil flow improver (LOFI) additives and were added to oil to improve the cold flow characteristics thereof. These compounds have not been used for a number of years and, due to the high chlorine content, these compounds would be considered unsuitable for use in a modern passenger car, or heavy duty diesel motor oil formulations. In modern formulations, these compounds have been supplanted by fumarate/vinyl acetate copolymers or polymethacrylate-based LOFIs.

U.S. Pat. No. 4,708,809 to Davis describes a lubricating oil composition containing a phenolic compound of the formula:

wherein R is a saturated hydrocarbon group having 10 or more aliphatic carbon atoms; a and b are each independently 1 to 3 times the number of aromatic nuclei present in Ar; and Ar is a single, fused or linked polynuclear ring moiety that is optionally substituted. It is alleged that the addition of a minor amount of such a compound to a lubricant composition that is mixed with fuel will lead to a reduction in piston ring sticking in a two cycle engine.

U.S. Pat. No. 6,495,496 to Gutierrez et al. describes nitrogen-containing low molecular weight Mannich base condensates of hydroxy aromatic compounds, an aldehyde and an amine that are useful as soot dispersants in lubricating oils.

U.S. Pat. No. 6,750,183 to Gutierrez et al. discloses certain oligomers useful as soot dispersants, which oligomers are defined by the formula:

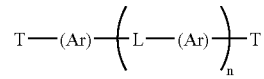

wherein each Ar independently represents an aromatic moiety optionally substituted by 1 to 6 substituents selected from H, $-OR_1$, $-N(R_1)_2$, F, Cl, Br, I, $-(L-(Ar)-T)$, $-S(O)_w$ $R_1$, $-(CZ)_x-(Z)_y-R_1$ and $-(Z)_y-(CZ)_x-R_1$, wherein w is 0 to 3, each Z is independently O, $-N(R_1)_2$ or S, x and y are independently 0 or 1 and each $R_1$ is independently H or a linear or branched, saturated or unsaturated, optionally substituted, hydrocarbyl group having from 1 to about 200 carbon atoms; each L is independently a linking moiety comprising a carbon-carbon single bond or a linking group; each T is independently H, $OR_1$, $N(R_1)_2$, F, Cl, Br, I, $S(O)_wR_1$, $(CZ)_x-(Z)_y-R_1$ or $(Z)_y-(CZ)_x-R_1$, wherein $R_1$, w, x, y and Z are as defined above; and n is 2 to about 1000.

SUMMARY OF THE INVENTION

In accordance with a first aspect of the present invention, there is provided a class of novel linked aromatic compounds found to act as potent soot dispersants in lubricating oil compositions.

In accordance with a second aspect of the invention, there are provided lubricating oil compositions containing the novel compounds of the first aspect, which lubricating oil compositions are capable of providing excellent soot dispersing performance.

In accordance with a third aspect of the invention, there is provided a method of operating a compression ignited (diesel) engine equipped with an EGR system, which method includes the steps of lubricating the crankcase of such an engine with a lubricating oil composition of the second aspect, and operating the engine.

In accordance with a fourth aspect, there is provided a novel class of precursor compounds from which the compounds of the first aspect can be derived.

DETAILED DESCRIPTION OF THE INVENTION

Compounds useful as precursors from which a novel class of soot dispersants can be derived can be defined by the formula:

(I)

wherein each Ar independently represents an aromatic moiety having 0 to 3 substituents selected from the group consisting of alkyl, alkoxy, alkoxyalkyl, hydroxy, hydroxyalkyl, halo and combinations thereof; each L is independently a linking moiety comprising a carbon-carbon single bond or a linking group; each Y is independently a moiety of the formula $H(O(CR_2)_n)_yX—$, wherein X is selected from the group consisting of $(CR'_2)_z$, O and S; R and R' are each independently selected from H, $C_1$ to $C_6$ alkyl and aryl; z is 1 to 10; n is 0 to 10 when X is $(CR'_2)_z$, and 2 to 10 when X is O or S; and y is 1 to 30; each a is independently 0 to 3, with the proviso that at least one Ar moiety bears at least one group Y; and m is 1 to 100.

Aromatic moieties Ar of Formula I can be a mononuclear carbocyclic moiety (phenyl) or a polynuclear carbocyclic moiety. Polynuclear carbocyclic moieties may comprise two or more fused rings, each ring having 4 to 10 carbon atoms (e.g., naphthalene) or may be linked mononuclear aromatic moieties, such as biphenyl, or may comprise linked, fused rings (e.g., binaphthyl). Examples of suitable polynuclear carbocyclic aromatic moieties include naphthalene, anthracene, phenanthrene, cyclopentenophenanthrene, benzanthracene, dibenzanthracene, chrysene, pyrene, benzpyrene and coronene and dimer, trimer and higher polymers thereof. Ar can also represent a mono- or polynuclear heterocyclic moiety. Heterocyclic moieties Ar include those comprising one or more rings each containing 4 to 10 atoms, including one or more hetero atoms selected from N, O and S. Examples of suitable monocyclic heterocyclic aromatic moieties include pyrrole, furan, thiophene, imidazole, oxazole, thiazole, pyrazole, pyridine, pyrimidine and purine. Suitable polynuclear heterocyclic moieties Ar include, for example, quinoline, isoquinoline, carbazole, dipyridyl, cinnoline, phthalazine, quinazoline, quinoxaline and phenanthroline. Each aromatic moiety (Ar) may be independently selected such that all moieties Ar are the same or different. Polycyclic carbocyclic aromatic moieties are preferred. Most preferred are compounds of Formula I wherein each Ar is naphthalene. Each aromatic moiety Ar may independently be unsubstituted or substituted with 1 to 3 substituents selected from alkyl, alkoxy alkoxyalkyl, hydroxyl, hydroxyalkyl, halo, and combinations thereof. Preferably, each Ar is unsubstituted (except for group(s) Y and terminal groups).

Each linking group (L) may be the same or different, and can be a carbon to carbon single bond between the carbon atoms of adjacent moieties Ar, or a linking group. Suitable linking groups include alkylene linkages, ether linkages, diacyl linkages, ether-acyl linkages, amino linkages, amido linkages, carbamido linkages, urethane linkages, and sulfur linkage. Preferred linking groups are alkylene linkages such as —$CH_3CHC(CH_3)_2$—, or $C(CH_3)_2$—; diacyl linkages such as —COCO— or —$CO(CH_2)_4CO$—; and sulfur linkages, such as —$S_1$— or —$S_x$—. More preferred linking groups are alkylene linkages, most preferably —$CH_2$—.

Preferably, Ar of Formula (I) represents naphthalene, and more preferably, Ar is derived from 2-(2-naphthyloxy)-ethanol. Preferably, each Ar is derived from 2-(2-naphthyloxy)-ethanol, and m is 2 to 25. Preferably, Y of Formula (I) is the group $H(O(CR_2)_2)_yO$—, wherein y is 1 to 6. More preferably, Ar is naphthalene, Y is $HOCH_2CH_2O$— and L is —$CH_2$—.

Methods for forming compounds of Formula I should be apparent to those skilled in the art. A hydroxyl aromatic compound, such as naphthol can be reacted with an alkylene carbonate (e.g., ethylene carbonate) to provide a compound of the formula AR—$(Y)_a$. Preferably, the hydroxyl aromatic compound and alkylene carbonate are reacted in the presence of a base catalyst, such as aqueous sodium hydroxide, and at a temperature of from about 25 to about 300° C., preferably at a temperature of from about 50 to about 200° C. During the reaction, water may be removed from the reaction mixture by azeotropic distillation or other conventional means. If separation of the resulting intermediate product is desired, upon completion of the reaction (indicated by the cessation of $CO_2$ evolution), the reaction product can be collected, and cooled to solidify. Alternatively, a hydroxyl aromatic compound, such as naphthol, can be reacted with an epoxide, such as ethylene oxide, propylene oxide, butylenes oxide or styrene oxide, under similar conditions to incorporate one or more oxy-alkylene groups.

To form a compound of Formula I, the resulting intermediate compound Ar—$(Y)_a$ may be further reacted with a polyhalogenated (preferably dihalogenated) hydrocarbon (e.g., 1-4-dichlorobutane, 2,2-dichloropropane, etc.), or a di- or poly-olefin (e.g., butadiene, isoprene, divinylbenzene, 1,4-hexadiene, 1,5-hexadiene, etc.) to yield a compound of Formula I having an alkylene linking groups. Reaction of moieties Ar—$(Y)_a$ and a ketone or aldehyde (e.g., formaldehyde, acetone, benzophenone, acetophenone, etc.) provides an alkylene linked compound. An acyl-linked compound can be formed by reacting moieties Ar—$(Y)_a$ with a diacid or anhydride (e.g., oxalic acid, malonic acid, succinic acid, glutaric acid, adipic acid, succinic anhydride, etc.). Sulfide, polysulfide, sulfinyl and sulfonyl linkages may be provided by reaction of the moieties Ar—$(Y)_a$ with a suitable difunctional sulfurizing agent (e.g., sulfur monochloride, sulfur dichloride, thionyl chloride ($SOCl_2$), sulfuryl chloride ($SO_2Cl_2$), etc.). To provide a compound of Formula I with an alkylene ether linkage, moieties Ar—$(Y)_a$ can be reacted with a divinylether. Compounds of Formula I, wherein L is a direct carbon to carbon link, may be formed via oxidative coupling polymerization using a mixture of aluminum chloride and cuprous chloride, as described, for example, by P. Kovacic, et al., *J. Polymer Science: Polymer Chem. Ed.*, 21, 457 (1983). Alternatively, such compounds may be formed by reacting moieties Ar—$(Y)_a$ and an alkali metal as described, for example, in "Catalytic Benzene Coupling on Caesium/Nanoporous Carbon Catalysts", M. G. Stevens, K. M. Sellers, S. Subramoney and H. C. Foley, *Chemical Communications*, 2679-2680 (1988).

To form the preferred compounds of Formula (I), having an alkylene linking group, more preferably a methylene linking group, base remaining in the Ar—$(Y)_a$ reaction mixture can be neutralized with acid, preferably with an excess of acid (e.g., a sulfonic acid) and reacted with an aldehyde, preferably formaldehyde, and preferably in the presence of residual acid, to provide an alkylene, preferably methylene bridged compound of Formula (I). The degree of polymerization of the compounds of Formula I range from 2 to about 101 (corresponding to a value of m of from 1 to about 100), preferably from about 2 to about 50, most preferably from about 2 to about 25.

Compounds of the present invention useful as the soot dispersants can be formed by reacting a compound of Formula (I) with at least one of an acylating agent, an alkylating agent and an arylating agent, and are represented by the formula:

(II)

wherein each Y' is independently a moiety of the formula Z(O(CR$_2$)$_n$)$_y$X—; Z is an acyl group, an alkyl group or an aryl group or H, and Ar, L, X, R, z, n and y are the same as defined in Formula (I), with the proviso that, at least one Ar moiety bears at least one substituent group Y' in which Z is not H; and m is 1 to 100.

Suitable acylating agents include hydrocarbyl carbonic acid, hydrocarbyl carbonic acid halides, hydrocarbyl sulfonic acid and hydrocarbyl sulfonic acid halides, hydrocarbyl phosphoric acid and hydrocarbyl phosphoric halides, hydrocarbyl isocyanates and hydrocarbyl succinic acylating agents. Preferred acylating agents are C$_8$ and higher hydrocarbyl isocyanates, such as dodecyl isocyanate and hexadodecyl isocyanate and C$_8$ or higher hydrocarbyl acylating agents, more preferably polybutenyl succinic acylating agents such as polybutenyl, or polyisobutenyl succinic anhydride (PIBSA). Preferably the hydrocarbyl succinic acylating agent will have a number average molecular weight ($\overline{M}_n$) of from about 100 to 5000, preferably from about 200 to about 3000, more preferably from about 450 to about 2500. Preferred hydrocarbyl isocyanate acylating agent will have a number average molecular weight ($\overline{M}_n$) of from about 100 to 5000, preferably from about 200 to about 3000, more preferably from about 200 to about 2000.

Acylating agents can be prepared by conventional methods known to those skilled in the art, such as chlorine-assisted, thermal and radical grafting methods. The acylating agents can be mono- or polyfunctional. Preferably, the acylating agents have a functionality of less than 1.3. Acylating agents are used in the manufacture of dispersants, and a more detailed description of methods for forming acylating agents is described in the description of suitable dispersants, presented infra.

Suitable alkylating agents include C$_8$ to C$_{30}$ alkane alcohols, preferably C$_8$ to C$_{18}$ alkane alcohols. Suitable arylating agents include C$_8$ to C$_{30}$, preferably C$_8$ to C$_{18}$ alkane-substituted aryl mono- or polyhydroxide.

Molar amounts of the compound of Formula (I) and the acylating, alkylating and/or arylating agent can be adjusted such that all, or only a portion, such as 25% or more, 50% or more or 75% or more of groups Y are converted to groups Y'. In the case where the compound of Formula (I) has hydroxy and/or alkyl hydroxy substituents, and such compounds are reacted with an acylating group, it is possible that all or a portion of such hydroxy and/or alkylhydroxy substituents will be converted to acyloxy or acyloxy alkyl groups. In the case where the compound of Formula (I) has hydroxy and/or alkyl hydroxy substituents, and such compounds are reacted with an arylating group, it is possible that all or a portion of such hydroxy and/or alkylhydroxy substituents will be converted to aryloxy or aryloxy alkyl groups. Therefore, compounds of Formula (II) substituted with acyloxy, acyloxy alkyl, aryloxy and/or aryloxy alkyl groups are considered within the scope of the present invention. A salt form of compounds of Formula (II) in which Z is an acylating group, which salts result from neutralization with base (as may occur, for example, due to interaction with a metal detergent, either in an additive package or a formulated lubricant), is also considered to be within the scope of the invention.

Compounds of Formula (II) can be derived from the precursors of Formula (I) by reacting the precursors of Formula (I) with the acylating agent, preferably in the presence of a liquid acid catalyst, such as sulfonic acid, e.g., dodecyl benzene sulfonic acid, paratoluene sulfonic acid or polyphosphoric acid or a solid acid catalyst such as Amberlyst-15, Amberlyst-36, zeolites, mineral acid clay or tungsten polyphosphoric acid; at a temperature of from about 0 to about 300° C., preferably from about 50 to about 250° C. Under the above conditions, the preferred polybutenyl succinic acylating agents can form diesters, acid esters or lactone esters with the compound of Formula (I).

Compounds of Formula (II) can be derived from the precursors of Formula (I) by reacting the precursors of Formula (I) with the alkylating agent or arylating agent, preferably in the presence of triphenylphosphine and diethyl azodicarboxylate (DEAD), a liquid acid catalyst, such as sulfonic acid, e.g., dodecyl benzene sulfonic acid, paratoluene sulfonic acid or polyphosphoric acid or a solid acid catalyst such as Amberlyst-15, Amberlyst-36, zeolites, mineral acid clay or tungsten polyphosphoric acid; at a temperature of from about 0 to about 300° C., preferably from about 50 to about 250° C.

Lubricating oil compositions of the present invention comprise a major amount of an oil of lubricating viscosity and a minor amount of a soot dispersing compound of Formula (II). Preferably, lubricating oil compositions of the present invention will contain from about 0.005 to 15 mass %, preferably from about 0.1 to about 5 mass %, more preferably from about 0.5 to about 2 mass % of a compound of Formula (II).

Oils of lubricating viscosity useful in the context of the present invention may be selected from natural lubricating oils, synthetic lubricating oils and mixtures thereof. The lubricating oil may range in viscosity from light distillate mineral oils to heavy lubricating oils such as gasoline engine oils, mineral lubricating oils and heavy duty diesel oils. Generally, the viscosity of the oil ranges from about 2 centistokes to about 40 centistokes, especially from about 4 centistokes to about 20 centistokes, as measured at 100° C.

Natural oils include animal oils and vegetable oils (e.g., castor oil, lard oil); liquid petroleum oils and hydrorefined, solvent-treated or acid-treated mineral oils of the paraffinic, naphthenic and mixed paraffinic-naphthenic types. Oils of lubricating viscosity derived from coal or shale also serve as useful base oils.

Synthetic lubricating oils include hydrocarbon oils and halo-substituted hydrocarbon oils such as polymerized and interpolymerized olefins (e.g., polybutylenes, polypropylenes, propylene-isobutylene copolymers, chlorinated polybutylenes, poly(1-hexenes), poly(1-octenes), poly(1-decenes)); alkylbenzenes (e.g., dodecylbenzenes, tetradecylbenzenes, dinonylbenzenes, di(2-ethylhexyl)benzenes); polyphenyls (e.g., biphenyls, terphenyls, alkylated polyphenols); and alkylated diphenyl ethers and alkylated diphenyl sulfides and derivative, analogs and homologs thereof. Also useful are synthetic oils derived from a gas to liquid process from Fischer-Tropsch synthesized hydrocarbons, which are commonly referred to as gas to liquid, or "GTL" base oils.

Alkylene oxide polymers and interpolymers and derivatives thereof where the terminal hydroxyl groups have been modified by esterification, etherification, etc., constitute another class of known synthetic lubricating oils. These are exemplified by polyoxyalkylene polymers prepared by polymerization of ethylene oxide or propylene oxide, and the alkyl and aryl ethers of polyoxyalkylene polymers (e.g., methyl-polyiso-propylene glycol ether having a molecular weight of 1000 or diphenyl ether of poly-ethylene glycol having a molecular weight of 1000 to 1500); and mono- and polycarboxylic esters thereof, for example, the acetic acid esters, mixed $C_3$-$C_8$ fatty acid esters and $C_{13}$ oxo acid diester of tetraethylene glycol.

Another suitable class of synthetic lubricating oils comprises the esters of dicarboxylic acids (e.g., phthalic acid, succinic acid, alkyl succinic acids and alkenyl succinic acids, maleic acid, azelaic acid, suberic acid, sebasic acid, fumaric acid, adipic acid, linoleic acid dimer, malonic acid, alkylmalonic acids, alkenyl malonic acids) with a variety of alcohols (e.g., butyl alcohol, hexyl alcohol, dodecyl alcohol, 2-ethylhexyl alcohol, ethylene glycol, diethylene glycol monoether, propylene glycol). Specific examples of such esters includes dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, and the complex ester formed by reacting one mole of sebacic acid with two moles of tetraethylene glycol and two moles of 2-ethylhexanoic acid.

Esters useful as synthetic oils also include those made from $C_5$ to $C_{12}$ monocarboxylic acids and polyols and polyol esters such as neopentyl glycol, trimethylolpropane, pentaerythritol, dipentaerythritol and tripentaerythritol.

Silicon-based oils such as the polyalkyl-, polyaryl-, polyalkoxy- or polyaryloxysilicone oils and silicate oils comprise another useful class of synthetic lubricants; such oils include tetraethyl silicate, tetraisopropyl silicate, tetra-(2-ethylhexyl) silicate, tetra-(4-methyl-2-ethylhexyl)silicate, tetra-(p-tert-butyl-phenyl) silicate, hexa-(4-methyl-2-ethylhexyl)disiloxane, poly(methyl)siloxanes and poly(methylphenyl) siloxanes. Other synthetic lubricating oils include liquid esters of phosphorous-containing acids (e.g., tricresyl phosphate, trioctyl phosphate, diethyl ester of decylphosphonic acid) and polymeric tetrahydrofurans.

The oil of lubricating viscosity may comprise a Group I, Group II or Group III, base stock or base oil blends of the aforementioned base stocks. Preferably, the oil of lubricating viscosity is a Group II or Group III base stock, or a mixture thereof, or a mixture of a Group I base stock and one or more a Group II and Group III. Preferably, a major amount of the oil of lubricating viscosity is a Group II, Group III, Group IV or Group V base stock, or a mixture thereof. The base stock, or base stock blend preferably has a saturate content of at least 65%, more preferably at least 75%, such as at least 85%. Most preferably, the base stock, or base stock blend, has a saturate content of greater than 90%. Preferably, the oil or oil blend will have a sulfur content of less than 1%, preferably less than 0.6%, most preferably less than 0.4%, by weight.

Preferably the volatility of the oil or oil blend, as measured by the Noack volatility test (ASTM D5880), is less than or equal to 30%, preferably less than or equal to 25%, more preferably less than or equal to 20%, most preferably less than or equal 16%. Preferably, the viscosity index (VI) of the oil or oil blend is at least 85, preferably at least 100, most preferably from about 105 to 140.

Definitions for the base stocks and base oils in this invention are the same as those found in the American Petroleum Institute (API) publication "Engine Oil Licensing and Certification System", Industry Services Department, Fourteenth Edition, December 1996, Addendum 1, December 1998. Said publication categorizes base stocks as follows:

a) Group I base stocks contain less than 90 percent saturates and/or greater than 0.03 percent sulfur and have a viscosity index greater than or equal to 80 and less than 120 using the test methods specified in Table 1.

b) Group II base stocks contain greater than or equal to 90 percent saturates and less than or equal to 0.03 percent sulfur and have a viscosity index greater than or equal to 80 and less than 120 using the test methods specified in Table 1.

c) Group III base stocks contain greater than or equal to 90 percent saturates and less than or equal to 0.03 percent sulfur and have a viscosity index greater than or equal to 120 using the test methods specified in Table 1.

d) Group IV base stocks are polyalphaolefins (PAO).

e) Group V base stocks include all other base stocks not included in Group I, II, III, or IV.

TABLE I

Analytical Methods for Base Stock

| Property | Test Method |
| --- | --- |
| Saturates | ASTM D 2007 |
| Viscosity Index | ASTM D 2270 |
| Sulfur | ASTM D 2622 |
|  | ASTM D 4294 |
|  | ASTM D 4927 |
|  | ASTM D 3120 |

Lubricating oil compositions of the present invention may further contain one or more ashless dispersants, which effectively reduce formation of deposits upon use in gasoline and diesel engines, when added to lubricating oils. Ashless dispersants useful in the compositions of the present invention comprises an oil soluble polymeric long chain backbone having functional groups capable of associating with particles to be dispersed. Typically, such dispersants comprise amine, alcohol, amide or ester polar moieties attached to the polymer backbone, often via a bridging group. The ashless dispersant may be, for example, selected from oil soluble salts, esters, amino-esters, amides, imides and oxazolines of long chain hydrocarbon-substituted mono- and polycarboxylic acids or anhydrides thereof; thiocarboxylate derivatives of long chain hydrocarbons; long chain aliphatic hydrocarbons having polyamine moieties attached directly thereto; and Mannich condensation products formed by condensing a long chain substituted phenol with formaldehyde and polyalkylene polyamine.

Preferably, the ashless dispersant is a "high molecular weight" dispersant having a number average molecular weight ($\overline{M}_n$) greater than or equal to 4,000, such as between 4,000 and 20,000. The precise molecular weight ranges will depend on the type of polymer used to form the dispersant, the number of functional groups present, and the type of polar functional group employed. For example, for a polyisobutylene derivatized dispersant, a high molecular weight dispersant is one formed with a polymer backbone having a number average molecular weight of from about 1680 to about 5600. Typical commercially available polyisobutylene-based dispersants contain polyisobutylene polymers having a number average molecular weight ranging from about 900 to about 2300, functionalized by maleic anhydride (MW=98), and derivatized with polyamines having a molecular weight of from about 100 to about 350. Polymers of lower molecular weight may also be used to form high molecular weight dispersants by incorporating multiple polymer chains into the dispersant, which can be accomplished using methods that are know in the art.

Polymer molecular weight, specifically $\overline{M}_n$, can be determined by various known techniques. One convenient method is gel permeation chromatography (GPC), which additionally provides molecular weight distribution information (see W. W. Yau, J. J. Kirkland and D. D. Bly, "Modern Size Exclusion Liquid Chromatography", John Wiley and Sons, New York, 1979). If the molecular weight of an amine-containing dispersant (e.g., PIBSA-polyamine or PIBSA-PAM) is being determined, the presence of the amine may cause the dispersant to be adsorbed by the column, leading to an inaccurate molecular weight determination. Persons familiar with the operation of GPC equipment understand that this problem may be eliminated by using a mixed solvent system, such as tetrahydrofuran (THF) mixed with a minor amount of pyridine, as opposed to pure THF. The problem may also be addressed by capping the amine with acetic anhydride and correcting the molecular weight based on the number of capping groups. Another useful method for determining molecular weight, particularly for lower molecular weight polymers, is vapor pressure osmometry (see, e.g., ASTM D3592).

The degree of polymerization $D_p$ of a polymer is:

$$D_p = \sum_i \frac{Mn \times mol. \ \% \ monomer \ i}{100 \times mol. \ wt \ monomer \ i}$$

and thus for the copolymers of two monomers $D_p$ may be calculated as follows:

$$D_p = \frac{Mn \times mol. \ \% \ monomer \ 1}{100 \times mol. \ wt \ monomer \ 1} + \frac{Mn \times mol. \ \% \ monomer \ 2}{100 \times mol. \ wt \ monomer \ 2}$$

Preferably, the degree of polymerization for the polymer backbones used in the invention is at least 30, typically from 30 to 165, more preferably 35 to 100.

The preferred hydrocarbons or polymers employed in this invention include homopolymers, interpolymers or lower molecular weight hydrocarbons. One family of useful polymers comprise polymers of ethylene and/or at least one $C_3$ to $C_{28}$ alpha-olefin having the formula $H_2C=CHR^1$, wherein $R^1$ is straight or branched chain alkyl radical comprising 1 to 26 carbon atoms and wherein the polymer contains carbon-to-carbon unsaturation, preferably a high degree of terminal ethenylidene unsaturation. One preferred class of such polymers employed in this invention comprise interpolymers of ethylene and at least one alpha-olefin of the above formula, wherein $R^1$ is alkyl of from 1 to 18 carbon atoms, and more preferably is alkyl of from 1 to 8 carbon atoms, and more preferably still of from 1 to 2 carbon atoms. Therefore, useful alpha-olefin monomers and comonomers include, for example, propylene, butene-1, hexene-1, octene-1, 4-methylpentene-1, decene-1, dodecene-1, tridecene-1, tetradecene-1, pentadecene-1, hexadecene-l, heptadecene-1, octadecene-1, nonadecene-1, and mixtures thereof (e.g., mixtures of propylene and butene-1, and the like). Exemplary of such polymers are propylene homopolymers, butene-1 homopolymers, propylene-butene copolymers, ethylene-propylene copolymers, ethylene-butene-1 copolymers and the like, wherein the polymer contains at least some terminal and/or internal unsaturation. Preferred polymers are unsaturated copolymers of ethylene and propylene and ethylene and butene-1. The interpolymers of this invention may contain a minor amount, e.g. 0.5 to 5 mole % of a $C_4$ to $C_{18}$ non-conjugated diolefin comonomer. However, it is preferred that the polymers of this invention comprise only alpha-olefin homopolymers, interpolymers of alpha-olefin comonomers and interpolymers of ethylene and alpha-olefin comonomers. The molar ethylene content of the polymers employed in this invention is preferably in the range of 20 to 80%, and more preferably 30 to 70%. When propylene and/or butene-1 are employed as comonomer(s) with ethylene, the ethylene content of such copolymers is most preferably between 45 and 65%, although higher or lower ethylene contents may be present.

These polymers may be prepared by polymerizing alpha-olefin monomer, or mixtures of alpha-olefin monomers, or mixtures comprising ethylene and at least one $C_3$ to $C_{28}$ alpha-olefin monomer, in the presence of a catalyst system comprising at least one metallocene (e.g., a cyclopentadienyl-transition metal compound) and an alumoxane compound. Using this process, a polymer in which 95% or more of the polymer chains possess terminal ethenylidene-type unsaturation can be provided. The percentage of polymer chains exhibiting terminal ethenylidene unsaturation may be determined by FTIR spectroscopic analysis, titration, or $C^{13}$ NMR. Interpolymers of this latter type may be characterized by the formula POLY-C($R^1$)=$CH_2$ wherein $R^1$ is $C_1$ to $C_{26}$ alkyl, preferably $C_1$ to $C_{18}$ alkyl, more preferably $C_1$ to $C_8$ alkyl, and most preferably $C_1$ to $C_2$ alkyl, (e.g., methyl or ethyl) and wherein POLY represents the polymer chain. The chain length of the $R^1$ alkyl group will vary depending on the comonomer(s) selected for use in the polymerization. A minor amount of the polymer chains can contain terminal ethenyl, i.e., vinyl, unsaturation, i.e. POLY-CH=$CH_2$, and a portion of the polymers can contain internal monounsaturation, e.g. POLY-CH=CH($R^1$), wherein $R^1$ is as defined above. These terminally unsaturated interpolymers may be prepared by known metallocene chemistry and may also be prepared as described in U.S. Pat. Nos. 5,498,809; 5,663,130; 5,705,577; 5,814,715; 6,022,929 and 6,030,930.

Another useful class of polymers is polymers prepared by cationic polymerization of isobutene, styrene, and the like. Common polymers from this class include polyisobutenes obtained by polymerization of a $C_4$ refinery stream having a butene content of about 35 to about 75% by wt., and an isobutene content of about 30 to about 60% by wt., in the presence of a Lewis acid catalyst, such as aluminum trichloride or boron trifluoride. A preferred source of monomer for making poly-n-butenes is petroleum feed streams such as Raffinate II. These feedstocks are disclosed in the art such as in U.S. Pat. No. 4,952,739. Polyisobutylene is a most preferred backbone of the present invention because it is readily available by cationic polymerization from butene streams (e.g., using $AlCl_3$ or $BF_3$ catalysts). Such polyisobutylenes generally contain residual unsaturation in amounts of about one ethylenic double bond per polymer chain, positioned along the chain.

As noted above, the polyisobutylene polymers employed are generally based on a hydrocarbon chain of from about 900 to 2,300. Methods for making polyisobutylene are known. Polyisobutylene can be functionalized by halogenation (e.g. chlorination), the thermal "ene" reaction, or by free radical grafting using a catalyst (e.g. peroxide), as described below.

Processes for reacting polymeric hydrocarbons with unsaturated carboxylic acids, anhydrides or esters and the preparation of derivatives from such compounds are disclosed in U.S. Pat. Nos. 3,087,936; 3,172,892; 3,215,707; 3,231,587; 3,272,746; 3,275,554; 3,381,022; 3,442,808; 3,565,804; 3,912,764; 4,110,349; 4,234,435; and GB-A-1,440,219. The polymer or hydrocarbon may be functionalized, for example, with carboxylic acid producing moieties (preferably acid or anhydride) by reacting the polymer or hydrocarbon under conditions that result in the addition of functional moieties or agents, i.e., acid, anhydride, ester moieties, etc., onto the polymer or hydrocarbon chains primarily at sites of carbonto-carbon unsaturation (also referred to as ethylenic or olefinic unsaturation) using the halogen assisted functionalization (e.g. chlorination) process or the thermal "ene" reaction.

When using the free radical grafting process employing a catalyst (e.g. peroxide), the functionalization is randomly effected along the polymer chain. Selective functionalization can be accomplished by halogenating, e.g., chlorinating or brominating the unsaturated α-olefin polymer to about 1 to 8 wt. %, preferably 3 to 7 wt. % chlorine, or bromine, based on the weight of polymer or hydrocarbon, by passing the chlorine or bromine through the polymer at a temperature of 60 to 250° C., preferably 110 to 160° C., e.g., 120 to 140° C., for about 0.5 to 10, preferably 1 to 7 hours. The halogenated polymer or hydrocarbon (hereinafter backbones) can then be reacted with sufficient monounsaturated reactant capable of adding functional moieties to the backbone, e.g., monounsaturated carboxylic reactant, at 100 to 250° C., usually about 180° C. to 235° C., for about 0.5 to 10, e.g., 3 to 8 hours, such that the product obtained will contain the desired number of moles of the monounsaturated carboxylic reactant per mole of the halogenated backbones. Alternatively, the backbone and the monounsaturated carboxylic reactant can be mixed and heated while adding chlorine to the hot material.

The hydrocarbon or polymer backbone can be functionalized, e.g., with carboxylic acid producing moieties (preferably acid or anhydride moieties) selectively at sites of carbon-to-carbon unsaturation on the polymer or hydrocarbon chains, or randomly along chains using the three processes mentioned above, or combinations thereof, in any sequence.

The preferred monounsaturated reactants that are used to functionalize the backbone comprise mono- and dicarboxylic acid material, i.e., acid, anhydride, or acid ester material, including (i) monounsaturated $C_4$ to $C_{10}$ dicarboxylic acid wherein (a) the carboxyl groups are vicinyl, (i.e., located on adjacent carbon atoms) and (b) at least one, preferably both, of said adjacent carbon atoms are part of said mono unsaturation; (ii) derivatives of (i) such as anhydrides or $C_1$ to $C_5$ alcohol derived mono- or diesters of (i); (iii) monounsaturated $C_3$ to $C_{10}$ monocarboxylic acid wherein the carbon-carbon double bond is conjugated with the carboxy group, i.e., of the structure —C=C—CO—; and (iv) derivatives of (iii) such as $C_1$ to $C_5$ alcohol derived mono- or diesters of (iii). Mixtures of monounsaturated carboxylic materials (i)-(iv) also may be used. Upon reaction with the backbone, the monounsaturation of the monounsaturated carboxylic reactant becomes saturated. Thus, for example, maleic anhydride becomes backbone-substituted succinic anhydride, and acrylic acid becomes backbone-substituted propionic acid. Exemplary of such monounsaturated carboxylic reactants are fumaric acid, itaconic acid, maleic acid, maleic anhydride, chloromaleic acid, chloromaleic anhydride, acrylic acid, methacrylic acid, crotonic acid, cinnamic acid, and lower alkyl (e.g., $C_1$ to $C_4$ alkyl) acid esters of the foregoing, e.g., methyl maleate, ethyl fumarate, and methyl fumarate. The monounsaturated carboxylic reactant, preferably maleic anhydride, typically will be used in an amount ranging from about 0.01 to about 20 wt. %, preferably 0.5 to 10 wt. %, based on the weight of the polymer or hydrocarbon.

While chlorination normally helps increase the reactivity of starting olefin polymers with monounsaturated functionalizing reactant, it is not necessary with the polymers or hydrocarbons contemplated for use in the present invention, particularly those preferred polymers or hydrocarbons which possess a high terminal bond content and reactivity. Preferably, therefore, the backbone and the monounsaturated functionality reactant, e.g., carboxylic reactant, are contacted at elevated temperature to cause an initial thermal "ene" reaction to take place. Ene reactions are known.

The hydrocarbon or polymer backbone can be functionalized by random attachment of functional moieties along the polymer chains by a variety of methods. For example, the polymer, in solution or in solid form, may be grafted with the monounsaturated carboxylic reactant, as described above, in the presence of a free-radical initiator. When performed in solution, the grafting takes place at an elevated temperature in the range of about 100 to 260° C., preferably 120 to 240° C. Preferably, free-radical initiated grafting is accomplished in a mineral lubricating oil solution containing, for example, 1 to 50 wt. %, preferably 5 to 30 wt. % polymer based on the initial total oil solution.

The free-radical initiators that may be used are peroxides, hydroperoxides, and azo compounds, preferably those that have a boiling point greater than about 100° C. and decompose thermally within the grafting temperature range to provide free-radicals. Representative of these free-radical initiators are azobutyronitrile, bis-tertiary-butyl peroxide and dicumene peroxide. The initiator, when used, typically is used in an amount of between 0.005% and 1% by weight based on the weight of the reaction mixture solution. Typically, the aforesaid monounsaturated carboxylic reactant material and free-radical initiator are used in a weight ratio range of from about 1.0:1 to 30:1, preferably 3:1 to 6:1. The grafting is preferably carried out in an inert atmosphere, such as under nitrogen blanketing. The resulting grafted polymer is characterized by having carboxylic acid (or ester or anhydride) moieties randomly attached along the polymer chains: it being understood, of course, that some of the polymer chains remain ungrafted. The free radical grafting described above can be used for the other polymers and hydrocarbons of the present invention.

The functionalized oil-soluble polymeric hydrocarbon backbone may then be further derivatized with a nucleophilic reactant, such as an amine, amino-alcohol, alcohol, metal compound, or mixture thereof, to form a corresponding derivative. Useful amine compounds for derivatizing functionalized polymers comprise at least one amine and can comprise one or more additional amine or other reactive or polar groups. These amines may be hydrocarbyl amines or may be predominantly hydrocarbyl amines in which the hydrocarbyl group includes other groups, e.g., hydroxy groups, alkoxy groups, amide groups, nitriles, imidazoline groups, and the like. Particularly useful amine compounds include mono- and polyamines, e.g., polyalkene and polyoxyalkylene polyamines of about 2 to 60, such as 2 to 40 (e.g., 3 to 20) total carbon atoms having about 1 to 12, such as 3 to 12, and preferably 3 to 9 nitrogen atoms per molecule. Mixtures of amine compounds may advantageously be used, such as those prepared by reaction of alkylene dihalide with ammonia. Preferred amines are aliphatic saturated amines, including, for example, 1,2-diaminoethane; 1,3-diaminopropane; 1,4-diaminobutane; 1,6-diaminohexane; polyethylene amines such as diethylene triamine; triethylene tetramine; tetraethylene pentamine; and polypropyleneamines such as 1,2-propylene diamine; and di-(1,2-propylene)triamine.

Other useful amine compounds include: alicyclic diamines such as 1,4-di(aminomethyl) cyclohexane and heterocyclic nitrogen compounds such as imidazolines. Another useful class of amines is the polyamido and related amido-amines as disclosed in U.S. Pat. Nos. 4,857,217; 4,956,107; 4,963,275; and 5,229,022. Also usable is tris(hydroxymethyl)amino methane (TAM) as described in U.S. Pat. Nos. 4,102,798; 4,113,639; 4,116,876; and UK 989,409. Dendrimers, star-like amines, and comb-structured amines may also be used.

Similarly, one may use condensed amines, as described in U.S. Pat. No. 5,053,152. The functionalized polymer is reacted with the amine compound using conventional techniques as described, for example, in U.S. Pat. Nos. 4,234,435 and 5,229,022, as well as in EP-A-208,560.

The functionalized, oil-soluble polymeric hydrocarbon backbones may also be derivatized with hydroxy compounds such as monohydric and polyhydric alcohols, or with aromatic compounds such as phenols and naphthols. Preferred polyhydric alcohols include alkylene glycols in which the alkylene radical contains from 2 to 8 carbon atoms. Other useful polyhydric alcohols include glycerol, mono-oleate of glycerol, monostearate of glycerol, monomethyl ether of glycerol, pentaerythritol, dipentaerythritol, and mixtures thereof. An ester dispersant may also be derived from unsaturated alcohols, such as allyl alcohol, cinnamyl alcohol, propargyl alcohol, 1-cyclohexene-3-ol, and oleyl alcohol. Still other classes of alcohols capable of yielding ashless dispersants comprise ether-alcohols, including oxy-alkylene and oxy-arylene. Such ether-alcohols are exemplified by ether-alcohols having up to 150 oxy-alkylene radicals in which the alkylene radical contains from 1 to 8 carbon atoms. The ester dispersants may be di-esters of succinic acids or acid-esters, i.e., partially esterified succinic acids, as well as partially esterified polyhydric alcohols or phenols, i.e., esters having free alcohols or phenolic hydroxy radicals. An ester dispersant may be prepared by any one of several known methods as described, for example, in U.S. Pat. No. 3,381,022.

Preferred groups of dispersant include polyamine-derivatized poly α-olefin, dispersants, particularly ethylene/butene alpha-olefin and polyisobutylene-based dispersants. Particularly preferred are ashless dispersants derived from polyisobutylene substituted with succinic anhydride groups and reacted with polyethylene amines, e.g., polyethylene diamine, tetraethylene pentamine; or a polyoxyalkylene polyamine, e.g., polyoxypropylene diamine, trimethylolaminomethane; a hydroxy compound, e.g., pentaerythritol; and combinations thereof. One particularly preferred dispersant combination is a combination of (A) polyisobutylene substituted with succinic anhydride groups and reacted with (B) a hydroxy compound, e.g., pentaerythritol; (C) a polyoxyalkylene polyamine, e.g., polyoxypropylene diamine, or (D) a polyalkylene diamine, e.g., polyethylene diamine and tetraethylene pentamine using about 0.3 to about 2 moles of (B), (C) and/or (D) per mole of (A). Another preferred dispersant combination comprises a combination of (A) polyisobutenyl succinic anhydride with (B) a polyalkylene polyamine, e.g., tetraethylene pentamine, and (C) a polyhydric alcohol or polyhydroxy-substituted aliphatic primary amine, e.g., pentaerythritol or trimethylolaminomethane, as described in U.S. Pat. No. 3,632,511.

Another class of ashless dispersants comprises Mannich base condensation products. Generally, these products are prepared by condensing about one mole of an alkyl-substituted mono- or polyhydroxy benzene with about 1 to 2.5 moles of carbonyl compound(s) (e.g., formaldehyde and paraformaldehyde) and about 0.5 to 2 moles of polyalkylene polyamine, as disclosed, for example, in U.S. Pat. No. 3,442,808. Such Mannich base condensation products may include a polymer product of a metallocene catalyzed polymerization as a substituent on the benzene group, or may be reacted with a compound containing such a polymer substituted on a succinic anhydride in a manner similar to that described in U.S. Pat. No. 3,442,808. Examples of functionalized and/or derivatized olefin polymers synthesized using metallocene catalyst systems are described in the publications identified supra.

The dispersant can be further post treated by a variety of conventional post treatments such as boration, as generally taught in U.S. Pat. Nos. 3,087,936 and 3,254,025. Boration of the dispersant is readily accomplished by treating an acyl nitrogen-containing dispersant with a boron compound such as boron oxide, boron halide boron acids, and esters of boron acids, in an amount sufficient to provide from about 0.1 to about 20 atomic proportions of boron for each mole of acylated nitrogen composition. Useful dispersants contain from about 0.05 to about 2.0 mass %, e.g., from about 0.05 to about 0.7 mass % boron. The boron, which appears in the product as dehydrated boric acid polymers (primarily $(HBO_2)_3$), is believed to attach to the dispersant imides and diimides as amine salts, e.g., the metaborate salt of the diimide. Boration can be carried out by adding from about 0.5 to 4 mass %, e.g., from about 1 to about 3 mass % (based on the mass of acyl nitrogen compound) of a boron compound, preferably boric acid, usually as a slurry, to the acyl nitrogen compound and heating with stirring at from about 135° C. to about 190° C., e.g., 140° C. to 170° C., for from about 1 to about 5 hours, followed by nitrogen stripping. Alternatively, the boron treatment can be conducted by adding boric acid to a hot reaction mixture of the dicarboxylic acid material and amine, while removing water. Other post reaction processes commonly known in the art can also be applied.

The dispersant may also be further post treated by reaction with a so-called "capping agent". Conventionally, nitrogen-containing dispersants have been "capped" to reduce the adverse effect such dispersants have on the fluoroelastomer engine seals. Numerous capping agents and methods are known. Of the known "capping agents", those that convert basic dispersant amino groups to non-basic moieties (e.g., amido or imido groups) are most suitable. The reaction of a nitrogen-containing dispersant and alkyl acetoacetate (e.g., ethyl acetoacetate (EAA)) is described, for example, in U.S. Pat. Nos. 4,839,071; 4,839,072 and 4,579,675. The reaction of a nitrogen-containing dispersant and formic acid is described, for example, in U.S. Pat. No. 3,185,704. The reaction product of a nitrogen-containing dispersant and other suitable capping agents are described in U.S. Pat. Nos. 4,663,064 (glycolic acid); 4,612,132; 5,334,321; 5,356,552; 5,716,912; 5,849,676; 5,861,363 (alkyl and alkylene carbonates, e.g., ethylene carbonate); 5,328,622 (mono-epoxide); 5,026,495; 5,085,788; 5,259,906; 5,407,591 (poly (e.g., bis)-epoxides) and 4,686,054 (maleic anhydride or succinic anhydride). The foregoing list is not exhaustive and other methods of capping nitrogen-containing dispersants are known to those skilled in the art.

For adequate piston deposit control, a nitrogen-containing dispersant can be added in an amount providing the lubricating oil composition with from about 0.03 mass % to about 0.15 mass %, preferably from about 0.07 to about 0.12 mass %, of nitrogen.

Additional additives may be incorporated in the compositions of the invention to enable them to meet particular requirements. Examples of additives which may be included in the lubricating oil compositions are detergents, metal rust inhibitors, viscosity index improvers, corrosion inhibitors, oxidation inhibitors, friction modifiers, other dispersants, anti-foaming agents, anti-wear agents and pour point depressants. Some are discussed in further detail below.

Metal-containing or ash-forming detergents function both as detergents to reduce or remove deposits and as acid neutralizers or rust inhibitors, thereby reducing wear and corrosion and extending engine life. Detergents generally comprise a polar head with a long hydrophobic tail, with the polar head comprising a metal salt of an acidic organic compound.

The salts may contain a substantially stoichiometric amount of the metal in which case they are usually described as normal or neutral salts, and would typically have a total base number or TBN (as can be measured by ASTM D2896) of from 0 to 80. A large amount of a metal base may be incorporated by reacting excess metal compound (e.g., an oxide or hydroxide) with an acidic gas (e.g., carbon dioxide). The resulting overbased detergent comprises neutralized detergent as the outer layer of a metal base (e.g. carbonate) micelle. Such overbased detergents may have a TBN of 150 or greater, and typically will have a TBN of from 250 to 450 or more.

Detergents that may be used include oil-soluble neutral and overbased sulfonates, phenates, sulfurized phenates, thiophosphonates, salicylates, and naphthenates and other oil-soluble carboxylates of a metal, particularly the alkali or alkaline earth metals, e.g., sodium, potassium, lithium, calcium, and magnesium. The most commonly used metals are calcium and magnesium, which may both be present in detergents used in a lubricant, and mixtures of calcium and/or magnesium with sodium. Particularly convenient metal detergents are neutral and overbased calcium sulfonates having TBN of from 20 to 450 TBN, and neutral and overbased calcium phenates and sulfurized phenates having TBN of from 50 to 450. Combinations of detergents, whether overbased or neutral or both, may be used.

Sulfonates may be prepared from sulfonic acids which are typically obtained by the sulfonation of alkyl substituted aromatic hydrocarbons such as those obtained from the fractionation of petroleum or by the alkylation of aromatic hydrocarbons. Examples included those obtained by alkylating benzene, toluene, xylene, naphthalene, diphenyl or their halogen derivatives such as chlorobenzene, chlorotoluene and chloronaphthalene. The alkylation may be carried out in the presence of a catalyst with alkylating agents having from about 3 to more than 70 carbon atoms. The alkaryl sulfonates usually contain from about 9 to about 80 or more carbon atoms, preferably from about 16 to about 60 carbon atoms per alkyl substituted aromatic moiety.

The oil soluble sulfonates or alkaryl sulfonic acids may be neutralized with oxides, hydroxides, alkoxides, carbonates, carboxylate, sulfides, hydrosulfides, nitrates, borates and ethers of the metal. The amount of metal compound is chosen having regard to the desired TBN of the final product but typically ranges from about 100 to 220 mass % (preferably at least 125 mass %) of that stoichiometrically required.

Metal salts of phenols and sulfurized phenols are prepared by reaction with an appropriate metal compound such as an oxide or hydroxide and neutral or overbased products may be obtained by methods well known in the art. Sulfurized phenols may be prepared by reacting a phenol with sulfur or a sulfur containing compound such as hydrogen sulfide, sulfur monohalide or sulfur dihalide, to form products which are generally mixtures of compounds in which 2 or more phenols are bridged by sulfur containing bridges.

Dihydrocarbyl dithiophosphate metal salts are frequently used as antiwear and antioxidant agents. The metal may be an alkali or alkaline earth metal, or aluminum, lead, tin, molybdenum, manganese, nickel or copper. The zinc salts are most commonly used in lubricating oil in amounts of 0.1 to 10, preferably 0.2 to 2 wt. %, based upon the total weight of the lubricating oil composition. They may be prepared in accordance with known techniques by first forming a dihydrocarbyl dithiophosphoric acid (DDPA), usually by reaction of one or more alcohol or a phenol with $P_2S_5$ and then neutralizing the formed DDPA with a zinc compound. For example, a dithiophosphoric acid may be made by reacting mixtures of primary and secondary alcohols. Alternatively, multiple dithiophosphoric acids can be prepared where the hydrocarbyl groups on one are entirely secondary in character and the hydrocarbyl groups on the others are entirely primary in character. To make the zinc salt, any basic or neutral zinc compound could be used but the oxides, hydroxides and carbonates are most generally employed. Commercial additives frequently contain an excess of zinc due to the use of an excess of the basic zinc compound in the neutralization reaction.

The preferred zinc dihydrocarbyl dithiophosphates are oil soluble salts of dihydrocarbyl dithiophosphoric acids and may be represented by the following formula:

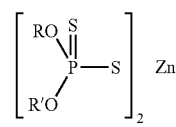

wherein R and R' may be the same or different hydrocarbyl radicals containing from 1 to 18, preferably 2 to 12, carbon atoms and including radicals such as alkyl, alkenyl, aryl, arylalkyl, alkaryl and cycloaliphatic radicals. Particularly preferred as R and R' groups are alkyl groups of 2 to 8 carbon atoms. Thus, the radicals may, for example, be ethyl, n-propyl, i-propyl, n-butyl, i-butyl, sec-butyl, amyl, n-hexyl, i-hexyl, n-octyl, decyl, dodecyl, octadecyl, 2-ethylhexyl, phenyl, butylphenyl, cyclohexyl, methylcyclopentyl, propenyl, butenyl. In order to obtain oil solubility, the total number of carbon atoms (i.e. R and R') in the dithiophosphoric acid will generally be about 5 or greater. The zinc dihydrocarbyl dithiophosphate can therefore comprise zinc dialkyl dithiophosphates. The present invention may be particularly useful when used with lubricant compositions containing phosphorus levels of from about 0.02 to about 0.12 mass %, such as from about 0.03 to about 0.10 mass %, or from about 0.05 to about 0.08 mass %, based on the total mass of the composition. In one preferred embodiment, lubricating oil compositions of the present invention contain zinc dialkyl dithiophate derived predominantly (e.g., over 50 mol. %, such as over 60 mol. %) from secondary alcohols.

Oxidation inhibitors or antioxidants reduce the tendency of mineral oils to deteriorate in service. Oxidative deterioration can be evidenced by sludge in the lubricant, varnish-like deposits on the metal surfaces, and by viscosity growth. Such oxidation inhibitors include hindered phenols, alkaline earth metal salts of alkylphenolthioesters having preferably $C_5$ to $C_{12}$ alkyl side chains, calcium nonylphenol sulfide, oil soluble phenates and sulfurized phenates, phosphosulfurized or sulfurized hydrocarbons, phosphorous esters, metal thiocarbamates, oil soluble copper compounds as described in U.S. Pat. No. 4,867,890, and molybdenum-containing compounds.

Typical oil soluble aromatic amines having at least two aromatic groups attached directly to one amine nitrogen contain from 6 to 16 carbon atoms. The amines may contain more than two aromatic groups. Compounds having a total of at least three aromatic groups in which two aromatic groups are linked by a covalent bond or by an atom or group (e.g., an oxygen or sulfur atom, or a —CO—, —$SO_2$— or alkylene group) and two are directly attached to one amine nitrogen also considered aromatic amines having at least two aromatic groups attached directly to the nitrogen. The aromatic rings are typically substituted by one or more substituents selected from alkyl, cycloalkyl, alkoxy, aryloxy, acyl, acylamino, hydroxy, and nitro groups.

Multiple antioxidants are commonly employed in combination. In one preferred embodiment, lubricating oil compositions of the present invention contain from about 0.1 to about 1.2 mass % of aminic antioxidant and from about 0.1 to about 3 mass % of phenolic antioxidant. In another preferred embodiment, lubricating oil compositions of the present invention contain from about 0.1 to about 1.2 mass % of aminic antioxidant, from about 0.1 to about 3 mass % of phenolic antioxidant and a molybdenum compound in an amount providing the lubricating oil composition from about 10 to about 1000 ppm of molybdenum.

Representative examples of suitable viscosity modifiers are polyisobutylene, copolymers of ethylene and propylene, polymethacrylates, methacrylate copolymers, copolymers of an unsaturated dicarboxylic acid and a vinyl compound, interpolymers of styrene and acrylic esters, and partially hydrogenated copolymers of styrene/isoprene, styrene/butadiene, and isoprene/butadiene, as well as the partially hydrogenated homopolymers of butadiene and isoprene.

Friction modifiers and fuel economy agents that are compatible with the other ingredients of the final oil may also be included. Examples of such materials include glyceryl monoesters of higher fatty acids, for example, glyceryl monooleate; esters of long chain polycarboxylic acids with diols, for example, the butane diol ester of a dimerized unsaturated fatty acid; oxazoline compounds; and alkoxylated alkyl-substituted mono-amines, diamines and alkyl ether amines, for example, ethoxylated tallow amine and ethoxylated tallow ether amine.

Other known friction modifiers comprise oil-soluble organo-molybdenum compounds. Such organo-molybdenum friction modifiers also provide antioxidant and antiwear credits to a lubricating oil composition. Examples of such oil soluble organo-molybdenum compounds include dithiocarbamates, dithiophosphates, dithiophosphinates, xanthates, thioxanthates, sulfides, and the like, and mixtures thereof. Particularly preferred are molybdenum dithiocarbamates, dialkyldithiophosphates, alkyl xanthates and alkylthioxanthates.

Additionally, the molybdenum compound may be an acidic molybdenum compound. These compounds will react with a basic nitrogen compound as measured by ASTM test D-664 or D-2896 titration procedure and are typically hexavalent. Included are molybdic acid, ammonium molybdate, sodium molybdate, potassium molybdate, and other alkaline metal molybdates and other molybdenum salts, e.g., hydrogen sodium molybdate, $MoOCl_4$, $MoO_2Br_2$, $Mo_2O_3Cl_6$, molybdenum trioxide or similar acidic molybdenum compounds.

Among the molybdenum compounds useful in the compositions of this invention are organo-molybdenum compounds of the formula

wherein R is an organo group selected from the group consisting of alkyl, aryl, aralkyl and alkoxyalkyl, generally of from 1 to 30 carbon atoms, and preferably 2 to 12 carbon atoms and most preferably alkyl of 2 to 12 carbon atoms. Especially preferred are the dialkyldithiocarbamates of molybdenum.

Another group of organo-molybdenum compounds useful in the lubricating compositions of this invention are trinuclear molybdenum compounds, especially those of the formula $Mo_3S_kL_nQ_z$ and mixtures thereof wherein the L are independently selected ligands having organo groups with a sufficient number of carbon atoms to render the compound soluble or dispersible in the oil, n is from 1 to 4, k varies from 4 through 7, Q is selected from the group of neutral electron donating compounds such as water, amines, alcohols, phosphines, and ethers, and z ranges from 0 to 5 and includes non-stoichiometric values. At least 21 total carbon atoms should be present among all the ligand organo groups, such as at least 25, at least 30, or at least 35 carbon atoms.

A viscosity index improver dispersant functions both as a viscosity index improver and as a dispersant. Examples of viscosity index improver dispersants include reaction products of amines, for example polyamines, with a hydrocarbyl-substituted mono -or dicarboxylic acid in which the hydrocarbyl substituent comprises a chain of sufficient length to impart viscosity index improving properties to the compounds. In general, the viscosity index improver dispersant may be, for example, a polymer of a $C_4$ to $C_{24}$ unsaturated ester of vinyl alcohol or a $C_3$ to $C_{10}$ unsaturated mono-carboxylic acid or a $C_4$ to $C_{10}$ di-carboxylic acid with an unsaturated nitrogen-containing monomer having 4 to 20 carbon atoms; a polymer of a $C_2$ to $C_{20}$ olefin with an unsaturated $C_3$ to $C_{10}$ mono- or di-carboxylic acid neutralised with an amine, hydroxyamine or an alcohol; or a polymer of ethylene with a $C_3$ to $C_{20}$ olefin further reacted either by grafting a $C_4$ to $C_{20}$ unsaturated nitrogen-containing monomer thereon or by grafting an unsaturated acid onto the polymer backbone and then reacting carboxylic acid groups of the grafted acid with an amine, hydroxy amine or alcohol.

Pour point depressants, otherwise known as lube oil flow improvers (LOFI), lower the minimum temperature at which the fluid will flow or can be poured. Such additives are well known. Typical of those additives that improve the low temperature fluidity of the fluid are $C_8$ to $C_{18}$ dialkyl fumarate/vinyl acetate copolymers, and polymethacrylates. Foam control can be provided by an antifoamant of the polysiloxane type, for example, silicone oil or polydimethyl siloxane.

Some of the above-mentioned additives can provide a multiplicity of effects; thus for example, a single additive may act as a dispersant-oxidation inhibitor. This approach is well known and need not be further elaborated herein.

In one preferred embodiment, lubricating oil compositions of the present invention further comprise, in combination with a compound of Formula (II), a high molecular weight polymer comprising (i) copolymers of hydrogenated poly (monovinyl aromatic hydrocarbon) and poly (conjugated diene), wherein the hydrogenated poly(monovinyl aromatic hydrocarbon) segment comprises at least about 20 wt. % of the copolymer; (ii) olefin copolymers containing alkyl or aryl amine, or amide groups, nitrogen-containing heterocyclic groups or ester linkages and/or (iii) acrylate or alkylacrylate copolymer derivatives having dispersing groups.

Copolymers of hydrogenated poly(monovinyl aromatic hydrocarbon) and poly (conjugated diene), wherein the hydrogenated poly(monovinyl aromatic hydrocarbon) segment comprises at least about 20 wt. % of the copolymer (hereinafter "Polymer (i)") are known viscosity modifiers and are commercially available as, for example, SV151 (Infineum USA L.P.). Preferred monovinyl aromatic hydrocarbon monomers useful in the formation of such materials include styrene, alkyl-substituted styrene, alkoxy-substituted styrene, vinyl naphthalene and alkyl-substituted vinyl naphthalene. The alkyl and alkoxy substituents may typically comprise from 1 to 6 carbon atoms, preferably from 1 to 4 carbon atoms. The number of alkyl or alkoxy substituents per molecule, if present, may range from 1 to 3, and is preferably one.

Preferred conjugated diene monomers useful in the formation of such materials include those conjugated dienes containing from 4 to 24 carbon atoms, such as 1,3-butadiene, isoprene, piperylene, methylpentadiene, 2-phenyl-1,3-butadiene, 3,4-dimethyl-1,3-hexadiene and 4,5-diethyl-1,3-octadiene.

Preferred are block copolymers comprising at least one poly(monovinyl aromatic hydrocarbon) block and at least one poly (conjugated diene) block. Preferred block copolymers are selected from those of the formula AB, wherein A represents a block polymer of predominantly poly(monovinyl aromatic hydrocarbon), B represents a block of predominantly poly (conjugated diene).

Preferably, the poly(conjugated diene) block is partially or fully hydrogenated. More preferably, the monovinyl aromatic hydrocarbons are styrene and/or alkyl-substituted styrene, particularly styrene. Preferred conjugated dienes are those containing from 4 to 12 carbon atoms, more preferably from 4 to 6 carbon atoms. Isoprene and butadiene are the most preferred conjugated diene monomers. Preferably, the poly (isoprene) is hydrogenated.

Block copolymers and selectively hydrogenated block copolymers are known in the art and are commercially available. Such block copolymers can be made can be made by anionic polymerization with an alkali metal initiator such as sec-butyllithium, as described, for example, in U.S. Pat. Nos. 4,764,572; 3,231,635; 3,700,633 and 5,194,530.

The poly(conjugated diene) block(s) of the block copolymer may be selectively hydrogenated, typically to a degree such that the residual ethylenic unsaturation of the block is reduced to at most 20%, more preferably at most 5%, most preferably at most 2% of the unsaturation level before hydrogenation. The hydrogenation of these copolymers may be carried out using a variety of well established processes including hydrogenation in the presence of such catalysts as Raney Nickel, noble metals such as platinum and the like, soluble transition metal catalysts and titanium catalysts as described in U.S. Pat. No. 5,299,464.

Sequential polymerization or reaction with divalent coupling agents can be used to form linear polymers. It is also known that a coupling agent can be formed in-situ by the polymerization of a monomer having two separately polymerizable vinyl groups such a divinylbenzene to provide star polymers having from about 6 to about 50 arms. Di- and multivalent coupling agents containing 2 to 8 functional groups, and methods of forming star polymers are well known and such materials are available commercially.

The second class of high molecular weight polymers are olefin copolymers (OCP) containing dispersing groups such as alkyl or aryl amnine, or amide groups, nitrogen-containing heterocyclic groups or ester linkages (hereinafter "Polymer (ii)"). These polymers have been used conventionally as multifunctional dispersant viscosity modifiers in lubricating oil compositions The olefin copolymers can comprise any combination of olefin monomers, but are most commonly ethylene and at least one other α-olefin. The at least one other α-olefin monomer is conventionally an α-olefin having 3 to 18 carbon atoms, and is most preferably propylene. As is well known, copolymers of ethylene and higher α-olefins, such as propylene, often include other polymerizable monomers. Typical of these other monomers are non-conjugated dienes such as the following, non-limiting examples a. straight chain dienes such as 1,4-hexadiene and 1,6-octadiene;
b. branched chain acyclic dienes such as 5-methyl-1,4-hexadiene; 3,7-dimethyl-1,6-octadiene; 3,7-dimethyl-1,7-octadiene and mixed isomers of dihydro-mycene and dihydroocinene;
c. single ring alicyclic dienes such as 1,4-cyclohexadiene; 1,5-cyclooctadiene; and 1,5-cyclododecadiene;
d. multi-ring alicyclic fused and bridged ring dienes such as tetrahydroindene;

methyltetrahydroindene; dicyclopentadiene; bicyclo-(2,2,1)-hepta-2,5-diene; alkenyl, alkylidene, cycloalkenyl and cycloalkylidene norbornenes such as 5-methylene -2-norbornene (MNB), 5-ethylidene-2-norbornene (ENB), 5-propylene -2-norbornene, 5-isoproylidene-2-norbornene, 5-(4-cyclopentyenyl) -2-norbornene; 5-cyclohexylidene-2-norbornene.

Of the non-conjugated dienes typically used, dienes containing at least one of the double bonds in a strained ring are preferred. The most preferred diene is 5-ethylidene-2-norbornene (ENB). The amount of diene (wt. basis) in the copolymer can be from 0% to about 20%, with 0% to about 15% being preferred, and 0% to about 10% being most preferred. As already noted, the most preferred olefin copolymer is ethylene-propylene. The average ethylene content of the copolymer can be as low as 20% on a weight basis. The preferred minimum ethylene content is about 25%. A more preferred minimum is 30%. The maximum ethylene content can be as high as 90% on a weight bas, preferably the maximum ethylene content is 85%, most preferably about 80%. Preferably, the olefin copolymers contain from about 35 to 75 wt. % ethylene, more preferably from about 50 to about 70 wt. % ethylene.

The molecular weight (number average) of the olefin copolymer can be as low as 2000, but the preferred minimum is 10,000. The more preferred minimum is 15,000, with the most preferred minimum number average molecular weight being 20,000. It is believed that the maximum number average molecular weight can be as high as 12,000,000. The preferred maximum is about 1,000,000, with the most preferred maximum being about 750,000. An especially preferred range of number average molecular weight for the olefin copolymers of the present invention is from about 50,000 to about 500,000.

Olefin copolymers can be rendered multifunctional by attaching a nitrogen-containing polar moiety (e.g., amine, amine-alcohol or amide) to the polymer backbone. The nitrogen-containing moieties are conventionally of the formula R—N—R'R", wherein R, R' and R" are independently alkyl, aryl of H. Also suitable are aromatic amines of the formula R—R'—NH—R"—R, wherein R' and R" are aromatic groups and each are is alkyl. The most common method for forming a multifunctional OCP viscosity modifier involves the free radical addition of the nitrogen-containing polar moiety to the polymer backbone. The nitrogen-containing polar moiety can be attached to the polymer using a double bond within the polymer (i.e., the double bond of the diene portion of an EPDM polymer, or by reacting the polymer with a compound providing a bridging group containing a double bond (e.g., maleic anhydride as described, for example, in U.S. Pat. Nos. 3,316,177; 3,326,804; and carboxylic acids and ketones as described, for example, in U.S. Pat. No. 4,068,056), and subsequently derivatizing the functionalized polymer with the nitrogen-containing polar moiety. A more complete list of nitrogen-containing compounds that can be reacted with the functionalized OCP are described infra, in the discussion of dispersants. Multifunctionalized OCPs and methods for forming such materials are known in the art and are available commercially (e.g., HITEC 5777 available from Afton Corporation and PA1160, a product of Dutch Staaten Minen).

Preferred are low ethylene olefin copolymers containing about 50 wt. % ethylene and having a number average molecular weight between 10,000 and 20,000 grafted with maleic anhydride and aminated with aminophenyldiamine and other dispersant amines.

The third class of polymers useful in the practice of the present invention are acrylate or alkylacrylate copolymer derivatives having dispersing groups (hereinafter "Polymer (iii)"). These polymers have been used as multifunctional dispersant viscosity modifiers in lubricating oil compositions, and lower molecular weight polymers of this type have been used as multifunctional dispersant/LOFIs. Such polymers are commercially available as, for example, ACRYLOID 954, (a product of RohMax USA Inc.) The acrylate or methacrylate monomers and alkyl acrylate or methacrylate monomers useful in the formation of Polymer (iii) can be prepared from the corresponding acrylic or methacrylic acids or their derivatives. Such acids can be derived using well known and conventional techniques. For example, acrylic acid can be prepared by acidic hydrolysis and dehydration of ethylene cyanohydrin or by the polymerization of β-propiolactone and the destructive distillation of the polymer to form acrylic acid. Methacrylic acid can be prepared by, for example, oxidizing a methyl α-alkyl vinyl ketone with metal hypochlorites; dehydrating hydroxyisobutyric acid with phosphorus pentoxide; or hydrolyzing acetone cyanohydrin.

Alkyl acrylates or methacrylate monomers can be prepared by reacting the desired primary alcohol with the acrylic acid or methacrylic acid in a conventional esterification catalyzed by acid, preferably p-toluene sulfonic acid and inhibited from polymerization by MEHQ or hydroquinone. Suitable alkyl acrylates or alkyl methacrylates contain from about 1 to about 30 carbon atoms in the alkyl carbon chain. Typical examples of starting alcohols include methyl alcohol, ethyl alcohol, ethyl alcohol, butyl alcohol, octyl alcohol, iso-octyl alcohol, isodecyl alcohol, undecyl alcohol, dodecyl alcohol, tridecyl alcohol, capryl alcohol, lauryl alcohol, myristyl alcohol, pentadecyl alcohol, palmityl alcohol and stearyl alcohol. The starting alcohol can be reacted with acrylic acid or methacrylic acid to form the desired acrylates and methacrylates, respectively. These acrylate polymers may have number average molecular weights ($\overline{M}_n$) of 10,000 to 1,000,000 and preferably the molecular weight range is from about 200,000 to 600,000.

To provide an acrylate or methacrylate with a dispersing group, the acrylate or methacrylate monomer is copolymerized with an amine-containing monomer or the acrylate or methacrylate main chain polymer is provided so as to contain sights suitable for grafting and then amine-containing branches are grafted onto the main chain by polymerizing amine-containing monomers.

Examples of amine-containing monomers include the basic amino substituted olefins such as p-(2-diethylaminoethyl) styrene; basic nitrogen-containing heterocycles having a polymerizable ethylenically unsaturated substituent such as the vinyl pyridines or the vinyl pyrrolidones; esters of amino alcohols with unsaturated carboxylic acids such as dimethylaminoethyl methacrylate and polymerizable unsaturated basic amines such as allyl amine.

Preferred Polymer (iii) materials include polymethacrylate copolymers made from a blend of alcohols with the average carbon number of the ester between 8 and 12 containing between 0.1-0.4% nitrogen by weight.

Most preferred are polymethacrylate copolymers made from a blend of alcohols with the average carbon number of the ester between 9 and 10 containing between 0.2-0.25% nitrogen by weight provided in the form of N-N Dimethylaminoalkyl-methacrylate.

Lubricating oil compositions useful in the practice of the present invention contain Polymer (i), (ii), (iii), or a mixture thereof, in an amount of from about 0.10 to about 2 wt. %, based on polymer weight; more preferably from about 0.2 to about 1 wt. %, most preferably from about 0.3 to about 0.8 wt. %. Alternatively in discussing the multifunctional components; specifically Polymers (ii) and (iii); said components are present providing nitrogen content to the lubricating oil composition from about 0.0001 to about 0.02 wt. %, preferably from about 0.0002 to about 0.01 wt. %, most preferably from about 0.0003 to about 0.008 wt. % of nitrogen. Polymers (i), (ii) (iii) and mixtures thereof, need not comprise the sole VM and/or LOFI in the lubricating oil composition, and other VM, such as non-functionalized olefin copolymer VM and, for example, alkylfumarate/vinyl acetate copolymer LOFIs may be used in combination therewith. For example, a heavy duty diesel engine of the present invention may be lubricated with a lubricating oil composition wherein the high molecular weight polymer is a mixture comprising from about 10 to about 90 wt. % of a hydrogenated styrene-isoprene block copolymer, and from about 10 to about 90 wt. % non-functionalized OCP.

In the present invention it may be necessary to include an additive which maintains the stability of the viscosity of the blend. Thus, although polar group-containing additives achieve a suitably low viscosity in the pre-blending stage it has been observed that some compositions increase in viscosity when stored for prolonged periods. Additives which are effective in controlling this viscosity increase include the long chain hydrocarbons functionalized by reaction with mono- or dicarboxylic acids or anhydrides which are used in the preparation of the ashless dispersants as hereinbefore disclosed.

When lubricating compositions contain one or more of the above-mentioned additives, each additive is typically blended into the base oil in an amount that enables the additive to provide its desired function.

When lubricating compositions contain one or more of the above-mentioned additives, each additive is typically blended into the base oil in an amount that enables the additive to provide its desired function. Representative effect amounts of such additives, when used in crankcase lubricants, are listed below. All the values listed are stated as mass percent active ingredient.

TABLE II

| ADDITIVE | MASS % (Broad) | MASS % (Preferred) |
| --- | --- | --- |
| Metal Detergents | 0.1-15 | 0.2-9 |
| Corrosion Inhibitor | 0-5 | 0-1.5 |
| Metal Dihydrocarbyl Dithiophosphate | 0.1-6 | 0.1-4 |
| Antioxidant | 0-5 | 0.01-3 |
| Pour Point Depressant | 0.01-5 | 0.01-1.5 |
| Antifoaming Agent | 0-5 | 0.001-0.15 |
| Supplemental Antiwear Agents | 0-1.0 | 0-0.5 |
| Friction Modifier | 0-5 | 0-1.5 |
| Viscosity Modifier | 0.01-10 | 0.25-3 |
| Basestock | Balance | Balance |

Fully formulated lubricating oil compositions of the present invention preferably have a sulfur content of less than about 0.4 mass %, more less than about 0.35 mass % more preferably less than about 0.03 mass %, such as less than about 0.15 mass %. Preferably, the Noack volatility of the fully formulated lubricating oil composition (oil of lubricating viscosity plus all additives) will be no greater than 13, such as no greater than 12, preferably no greater than 10. Fully formulated lubricating oil compositions of the present invention preferably have no greater than 1200 ppm of phosphorus, such as no greater than 1000 ppm of phosphorus, or no greater than 800 ppm of phosphorus. Fully formulated lubricating oil compositions of the present invention preferably have a sulfated ash (SASH) content of about 1.0 mass % or less.

It may be desirable, although not essential to prepare one or more additive concentrates comprising additives (concentrates sometimes being referred to as additive packages) whereby several additives can be added simultaneously to the oil to form the lubricating oil composition. A concentration for the preparation of a lubricating oil composition of the present invention may, for example, contain from about 0.15 to about 20 mass % of a compound of Formula (II); about 10 to about 40 mass % of a nitrogen-containing dispersant; about 2 to about 20 mass % of an aminic antioxidant, a phenolic antioxidant, a molybdenum compound, or a mixture thereof; about 5 to about 40 mass % of a detergent; and from about 2 to about 20 mass % of a metal dihydrocarbyl dithio phosphate.

The final composition may employ from 5 to 25 mass %, preferably 5 to 18 mass %, typically 10 to 15 mass % of the concentrate, the remainder being oil of lubricating viscosity and viscosity modifier.

All weight percents expressed herein (unless otherwise indicated) are based on active ingredient (A.I.) content of the additive, and/or upon the total weight of any additive-package, or formulation which will be the sum of the A.I. weight of each additive plus the weight of total oil or diluent.

This invention will be further understood by reference to the following examples, wherein all parts are parts by weight, unless otherwise noted.

EXAMPLES

Synthesis Example 1

Preparation of a compound of Formula (II)

Step 1 —Preparation of 2-(2-naphthyloxy) ethanol

A two-liter resin kettle equipped with mechanical stirrer, condenser/Dean-Stark trap, and inlets for nitrogen, was charged with 2-naphthol (600 g, 4.16 moles), ethylene carbonate (372 g, 4.22 moles) and xylene (200 g), and the mixture was heated to 90° C. under nitrogen. Aqueous sodium hydroxide (50 mass %, 3.0 g) was added and water was removed by azeotropic distillation at 165° C. The reaction mixture was kept at 165° C. for 2 hours. $CO_2$ evolved as the reaction progressed and the reaction was determined to be near completion when the evolution of $CO_2$ ceased. The product was collected and solidified while cooling to room temperature. The completion of reaction was confirmed by FT-IR and HPLC. The structure of the 2-(2-naphthyloxy) ethanol product was confirmed by 1H and $^{13}C$—NMR.

Step 2 —Oligomerization of 2-(2-naphthyloxy) ethanol

A two-liter resin kettle equipped with mechanical stirrer, condenser/Dean-Stark trap, and inlets for nitrogen, was charged with 2-(2-naphthyloxy) ethanol from Step 1, toluene (200 g), SA 117 (60.0 g), and the mixture was heated to 70° C. under nitrogen. Para-formaldehyde was added over 15 min at 70 -80° C., and heated to 90° C. and the reaction mixture was kept at that temperature for 30 min to 1 hour. The temperature was gradually increased to 110° C. to 120° C. over 2-3 hours and water (75-83 ml) was removed by azeotropic distillation. The polymer was collected and solidified while cooling to room temperature. $\overline{M}_n$ was determined by GPC using polystyrene standard corrected with the elution volume of 2-(2-naphthyloxy) ethanol as internal standard. THF was used as eluent. ($\overline{M}_n$ of 1000 dalton). $^1H$ and $^{13}C$ NMR confirmed the structure. FDMS and MALDI-TOF indicates the product contains mixture of methylene-linked 2-(2-naphthyloxy) ethanol oligomer of Formula (I) containing from 2 to 24 2-(2-naphthyloxy) ethanol units (m is 1 to 23).

Step 3 —Reaction of methylene-linked 2-(2-naphthyloxy) ethanol oligomer and an acylating agent (PIBSA)

A five-liter resin kettle equipped with mechanical stirrer, condenser/Dean-Stark trap, inlets for nitrogen, and additional funnel was charged with poly (2-(2-naphthyloxy) ethanol)-co-formaldehyde) from Step 2, toluene (200 g), and the mixture is heated to 120 ° C. under nitrogen. Polyisobutenyl succinic anhydride (PIBSA $\overline{M}$ of 450, 2,500 g) was added portion wise (~250 g at 30 min intervals) and the temperature was maintained at 120 ° C. for 2 hours followed by heating to 140 ° C. under nitrogen purge for an additional 2 hours to strip off all solvents to a constant weight. Base oil (AMEXOM 100 N, 1100 g) was added, and the product was collected at room temperature. GPC and FT-IR confirmed the desired structure.

The reaction scheme representing the above synthesis is shown below:

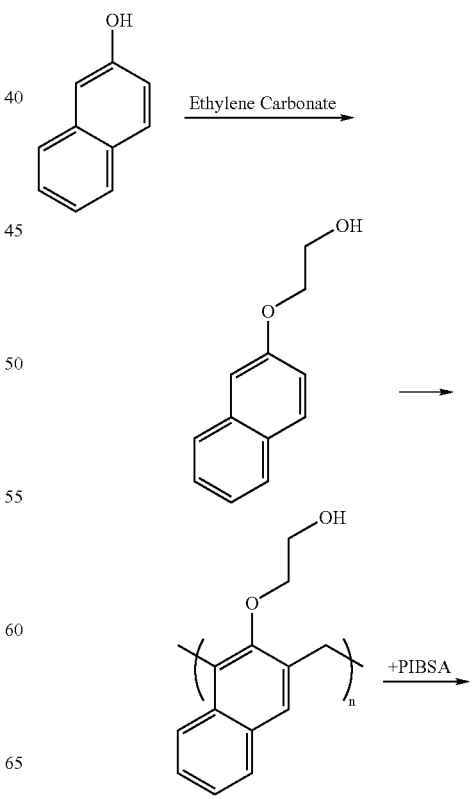

-continued

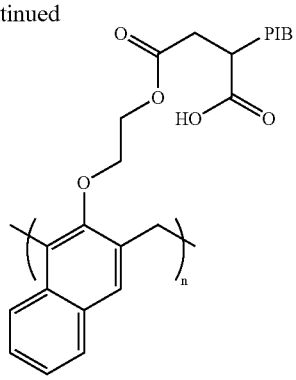

Performance Example 1

The soot dispersing performance of the compounds of Formula (II) was determined in a carbon black bench test (CBBT). In the CBBT, the ability of finished oil samples to disperse carbon black is evaluated by mixing the finished oil samples with increasing amounts of carbon black, stirring the samples overnight at 90° C., and evaluating the samples for viscosity and index using a rotational viscometer. The shear rate of the rotational viscometer is varied up to 300 sec.$^{-1}$ and a plot of shear vs. log viscosity is obtained. If the viscosity is Newtonian, the slope of the plot (the index) approaches unity, indicating that the soot remains well dispersed. If the index becomes significantly less than unity, there is shear thinning indicative of poor soot dispersancy.

A control sample representing a commercial, fully formulated "PC-9" heavy duty diesel (HDD) crankcase lubricant was prepared. The control sample (Comp. 1) contained a major amount of oil of lubricating viscosity; a viscosity modifier and an additive package including a high molecular weight dispersant, overbased detergent, an antiwear agent (ZDDP), ashless antioxidant and a flow improver (LOFI). The high molecular weight dispersant was added in an amount providing the fully formulated lubricant with a nitrogen content of about 0.09 mass %. A sample representing the invention (Inv. 1) was prepared by adding 2 mass % of the compound of Synthesis Example 1 to the control sample. Fresh samples and samples loaded with 8 and 12% carbon black were evaluated in the manner described above. The Index and Viscosity (expressed as cP) of the samples are shown below in Tables III and IV, respectively:

TABLE III

| | Index | |
|---|---|---|
| Mass % Carbon Black | Comp. 1 | Inv. 1 |
| 0 | 0.99 | 0.99 |
| 8 | 0.15 | 0.97 |
| 12 | TVTM* | 0.85 |

TABLE IV

| | Viscosity (cP) | |
|---|---|---|
| Mass % Carbon Black | Comp. 1 | Inv. 1 |
| 0 | 13.5 | 15.0 |
| 8 | 172.6 | 41.2 |
| 12 | TVTM* | 85.5 |

*too viscous to measure

As shown by the above data, the formulated lubricants containing the compound of Formula (II) provided improved index and viscosity in the presence of carbon black compared to the conventional lubricant.

Nitrogen in lubricating oil compositions is known to have adverse effects on conventional fluoroelastomer engines seals. Inclusion of a compound of Formula (II) in a lubricant also containing a nitrogen-containing dispersant has also been found to ameliorate these adverse effects. To demonstrate this effect, Comp. 1 and Inv. 1 were compared in a Daimler-Chrysler (Mercedes Benz) seals test using an AK6 seal material Daimler Chrysler Seals Test VDA 675301 ("closed cup"; seven days). AK6 is a Viton™ material; a fluoroelastomer material commonly used in vehicular engine seals. The results of the comparison are provided below, in Table V:

TABLE V

| Seal Compatibility Test | | | | |
|---|---|---|---|---|
| Property | Units | Pass | Comp. 1 | Inv. 1 |
| Tensile Strength | % change | −50 max | −33 | −17 |
| Elongation | % change | −55 | −35 | −14 |
| Hardness | % change | −5.0 to +5.0 | 0 | 1 |
| Volume | % change | 0 to +5 | 0.4 | 0.4 |

The improvement in seal compatibility achieved by the addition of a compound of Formula II is shown by the reduced change the tensile strength of the fluoroelastomer seal material at the conclusion of the test.

The disclosures of all patents, articles and other materials described herein are hereby incorporated, in their entirety, into this specification by reference. A description of a composition comprising, consisting of, or consisting essentially of multiple specified components, as presented herein and in the appended claims, should be construed to also encompass compositions made by admixing said multiple specified components. The principles, preferred embodiments and modes of operation of the present invention have been described in the foregoing specification. What applicants submit is their invention, however, is not to be construed as limited to the particular embodiments disclosed, since the disclosed embodiments are regarded as illustrative rather than limiting. Changes may be made by those skilled in the art without departing from the spirit of the invention.

What is claimed is:

1. A compound of the formula:

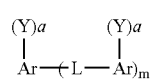
(I)

wherein:
each Ar independently represents a polycyclic carbocyclic aromatic moiety having 0 to 3 substituents selected from the group consisting of alkyl, alkoxy, alkoxyalkyl, hydroxy, hydroxyalkyl, halo and combinations thereof;
each L is independently a linking moiety comprising a linking group;
each Y is independently a moiety of the formula $H(OCR_2)_n)_yX-$, wherein X is selected from the group consisting of $(CR'_2)_z$, O and S; R and R' are each independently is selected from H, $C_1$ to $C_6$ alkyl and aryl; z is 1 to 10; n is 1 to 10 when X is $(CR'_2)_z$, and 2 to 10 when X is O or S; and y is 1 to 30;

each a is independently 0 to 3, with the proviso that at least one Ar moiety bears at least one group Y; and m is 2 to 25.

2. A compound of claim 1, wherein Y is $H(O(CR_2)_2)_yO$— and y is 1 to 6.

3. A compound of claim 2, wherein Ar is naphthalene, Y is $HOCH_2CH_2O$— and L is $CH_2$.

4. A compound of claim 3, wherein Ar is derived from 2-(2-naphthyloxy)-ethanol.

5. The reaction product of an acylating agent and a compound of the formula:

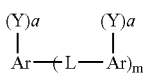
(I)

wherein:
each Ar independently represents a polycyclic carbocyclic aromatic moiety having 0 to 3 substituents selected from the group consisting of alkyl, alkoxy, alkoxyalkyl, hydroxy, hydroxyalkyl, halo and combinations thereof;
each L is independently a linking moiety comprising a linking group;
each Y is independently a moiety of the formula $H(O(CR_2)_n)_yX$—, wherein X is selected from the group consisting of $(CR'_2)_z$, O and S; R and R' are each independently selected from H, $C_1$ to $C_6$ alkyl and aryl; z is 1 to 10; n is 0 to 10 when X is $(CR'_2)_z$, and 2 to 10 when X is O or S; and y is 1 to 30;
each a is independently 0 to 3, with the proviso that at least one Ar moiety bears at least one group Y; and m is 1 to 100.

6. The reaction product of claim 5, wherein said acylating agent is a polyalkyl or polyalkenyl succinic acylating agent having $\overline{M}_n$ of from about 100 to about 5000.

7. The reaction product of claim 5, wherein said acylating agent is hydrocarbyl isocyanate.

8. The reaction product of a compound of claim 4 and a polyalkyl or polyalkenyl succinic acylating agent having $\overline{M}_n$ of from about 100 to about 5000.

9. The reaction product of a compound of claim 4, and hydrocarbyl isocyanate.

10. A process for forming a compound of claim 3 comprising reaction of naphthyloxyethanol with formaldehyde in the presence of acid to form a methylene-bridged naphthyloxyethanol compound.

11. The process of claim 10, wherein said naphthyloxyethanol is the product of a process comprising (i) reaction of a hydroxyl-naphthalene compound with ethylene carbonate in the presence of a base catalyst to form naphthyloxyethanol.

12. The process of claim 11, wherein remaining base is neutralized with an excess of acid prior to reaction with said formaldehyde.

13. The process of claim 10, wherein said acid is an oil soluble sulfonic acid or a solid acid catalyst.

14. A process for forming a reaction product of claim 8 comprising reaction of a methylene-bridged naphthyloxyethanol compound with a polyalkyl or polyalkenyl succinic acylating agent in the presence of an acid catalyst.

15. The process of claim 14, wherein said methylene-bridged naphthyloxyethanol compound is the product of a process comprising (i) reaction of a hydroxyl-naphthalene compound with ethylene carbonate in the presence of a base catalyst to form naphthyloxyethanol; (ii) neutralization of said base with an excess of acid to provide an intermediate; and (iii) reaction of said intermediate with formaldehyde in the presence of residual acid.

16. The process of claim 14, wherein said acid is an oil soluble liquid acid catalyst or a solid acid catalyst.

17. The process of claim 14, wherein said acylating agent is a polybutenyl succinic acylating agent having $\overline{M}_n$ of from about 300 to about 5000.

18. A process for forming a reaction product of claim 9 comprising reaction of a methylene-bridged naphthyloxyethanol compound and a hydrocarbyl isocyanate in the presence of an acid catalyst.

19. The process of claim 9, for forming a reaction product of claim 9, wherein said methylene-bridged naphthyloxyethanol compound is the product of a process comprising (i) reaction of a hydroxyl-naphthalene compound with ethylene carbonate in the presence of a base catalyst to form naphthyloxyethanol; (ii) neutralization of said base with an excess of acid to provide an intermediate; and (iii) reaction of said intermediate with formaldehyde in the presence of residual acid.

20. The process of claim 18, wherein said acid is an oil soluble liquid acid catalyst or a solid acid catalyst.

21. A compound of the formula:

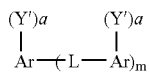
(II)

wherein:
each Ar independently represents a polycyclic carbocyclic aromatic moiety having 0 to 3 substituents selected from the group consisting of alkyl, alkoxy, alkoxyalkyl, hydroxy, hydroxyalkyl, acyloxy, acyloxyalkyl, aryloxy, aryloxy alkyl, halo and combinations thereof;
each L is independently a linking moiety comprising a carbon-carbon single bond or a linking group;
each Y is independently a moiety of the formula $Z(O(CR_2)_n)_yX$—, wherein X is selected from the group consisting of $(CR'_2)_z$, O and S; R and R' are each independently selected from H, $C_1$ to $C_6$ alkyl and aryl; z is 1 to 10; n is 1 to 10 when X is $(CR'_2)_z$, and 2 to 10 when X is O or S; y is 1 to 30; Z is H, an acyl group, an alkyl group or an aryl group;
each a is independently 0 to 3, with the proviso that at least one Ar moiety bears at least one group Y in which Z is not H; and m is 1 to 100.

22. A compound of claim 21, wherein Y is $Z(O(CR_2)_2)_yO$—, Z is an acyl group and y is 1 to 6.

23. A compound of claim 22, wherein Ar is naphthalene, Y is $ZOCH_2CH_2O$—, Z is an acyl group and L is $CH_2$.

24. A compound of claim 23, wherein Ar is derived from 2-(2-naphthyloxy)-ethanol and m is 2 to 25.

25. A compound of claim 21, wherein Z is derived from a polyalkyl or polyalkenyl succinic acylating agent having $\overline{M}_n$ of from about 100 to about 5000.

26. A compound of claim 23, wherein Z is derived from a polyalkyl or polyalkenyl succinic acylating agent having $\overline{M}_n$ of from about 100 to about 5000.

27. A compound of claim 21, wherein Z is derived from hydrocarbyl isocyanate.

28. A compound of claim 23, wherein Z is derived from hydrocarbyl isocyanate.

29. A lubricating oil composition comprising a major amount of an oil of lubricating viscosity and a minor amount of a compound of claim 21.

30. A lubricating oil composition of claim 29, further comprising a nitrogen-containing dispersant.

31. A lubricating oil composition of claim 30 comprising an amount of said nitrogen-containing dispersant providing said lubricating oil composition with from about 0.03 mass % to about 0.15 mass % of nitrogen and from about 0.005 to 15 mass % of said compound.

32. A lubricating oil composition of claim 30, wherein said nitrogen-containing dispersant is a polybutenyl polyalkyleneamine succinimide derived from polybutene having $\overline{M}_n$ of from about 900 to about 2500.

33. A lubricating oil composition of claim 32, wherein said polybutenyl polyalkyleneamine succinimide is post-reacted with at least one of (i) a bis-epoxide compound; and (ii) ethylene carbonate.

34. A lubricating oil composition of claim 30, further comprising at least one additional additive selected from the group consisting of detergents, antiwear agents, antioxidants, friction modifiers compatibilizers and viscosity modifiers.

35. A lubricating oil composition of claim 34, containing from about 0.1 to about 1.2 mass % of an aminic antioxidant and from about 0.1 to about 3 mass % of a phenolic antioxidant.

36. A lubricating oil composition of claim 35, further comprising a molybdenum compound in an amount introducing into said lubricating oil composition from about 10 to about 1000 ppm of molybdenum.

37. A lubricating oil composition of claim 34, comprising a metal dihydrocarbyl dithio phosphate derived predominantly from secondary alcohols.

38. A lubricating oil composition of claim 34, comprising no greater than about 1200 ppm of phosphorus.

39. A lubricating oil composition of claim 38, comprising no greater than about 1000 ppm of phosphorus.

40. A lubricating oil composition of claim 39, comprising no greater than about 800 ppm of phosphorus.

41. A lubricating oil composition of claim 34, having a sulfated ash content of no more than about 1 mass %.

42. A lubricating oil composition of claim 30, further comprising a minor amount of one or more high molecular weight polymers comprising (i) copolymers of hydrogenated poly (monovinyl aromatic hydrocarbon) and poly (conjugated diene), wherein the hydrogenated poly(monovinyl aromatic hydrocarbon) segment comprises at least about 20 wt. % of the copolymer; (ii) olefin copolymers containing alkyl or aryl amine, or amide groups, nitrogen-containing heterocyclic groups or ester linkages and/or (iii) acrylate or alkylacrylate copolymer derivatives having dispersing groups.

43. A lubricating oil composition of claim 29, wherein a major amount of the oil of lubricating viscosity is Group II, Group III, Group IV or Group V base stock, or a mixture thereof.

44. A lubricating oil composition of claim 29, wherein a major amount of the oil of lubricating viscosity is a base stock derived from a gas to liquid process.

45. A method of operating a compression ignited engine, which method comprises lubricating a crankcase of said engine with a lubricating oil composition of claim 29 and operating the engine.

46. The method of claim 45, wherein said compression ignited engine is provided with an exhaust gas recirculation system.

47. The method of claim 46, wherein said engine is a heavy duty diesel engine and said exhaust gas recirculation system cools intake air and/or exhaust gas recirculation streams to below the dew point for at least 10% of the time said engine is in operation.

48. A lubricating oil concentrate comprising from about 0.15 to about 20 mass % of a compound of claim 21; (ii) about 10 to about 40 mass % of a high molecular weight nitrogen-containing dispersant; (iii) about 2 to about 20 mass % of an aminic antioxidant, a phenolic antioxidant, a molybdenum compound, or a mixture thereof; (iv) about 5 to 40 mass % of a detergent; and (v) from about 2 to about 20 mass % of a metal dihydrocarbyl dithiophosphate.

* * * * *